United States Patent
Lim et al.

(10) Patent No.: US 11,744,457 B2
(45) Date of Patent: Sep. 5, 2023

(54) METHOD FOR MEASURING ANOMALIES OF REFRACTION USING A REFLECTION IMAGE OF PUPIL IN VISIBLE LIGHT

(71) Applicant: SAMSUNG LIFE PUBLIC WELFARE FOUNDATION, Seoul (KR)

(72) Inventors: Dong Hui Lim, Seoul (KR); Young Jun Kim, Busan (KR); Jae Hyeong Chun, Jeollabuk-do (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 472 days.

(21) Appl. No.: 17/136,174

(22) Filed: Dec. 29, 2020

(65) Prior Publication Data

US 2021/0259542 A1 Aug. 26, 2021

(30) Foreign Application Priority Data

Feb. 20, 2020 (KR) .......................... 10-2020-0021273

(51) Int. Cl.
| | |
|---|---|
| G06T 11/60 | (2006.01) |
| A61B 3/103 | (2006.01) |
| A61B 3/14 | (2006.01) |
| A61B 5/00 | (2006.01) |
| G06V 10/764 | (2022.01) |
| G06V 10/82 | (2022.01) |
| G06V 10/44 | (2022.01) |

(52) U.S. Cl.
CPC ................ *A61B 3/103* (2013.01); *A61B 3/14* (2013.01); *A61B 5/7267* (2013.01); *G06T 11/60* (2013.01); *G06V 10/454* (2022.01); *G06V 10/764* (2022.01); *G06V 10/82* (2022.01)

(58) Field of Classification Search
CPC .......................... A61B 5/7267; G06T 711/60
See application file for complete search history.

(56) References Cited

U.S. PATENT DOCUMENTS

| | | | | |
|---|---|---|---|---|
| 6,089,715 A | * | 7/2000 | Hoover | A61B 3/113 351/221 |
| 2022/0304572 A1 | * | 9/2022 | Coveney | G06T 7/0012 |

OTHER PUBLICATIONS

Chun et al. "A Deep-Learning-Based Prediction of Refractive Error Using Photorefraction Images Captured by Smartphone" American Academy of Ophthalmology Conference, Oct. 12-15, 2019 (14 pages).

* cited by examiner

*Primary Examiner* — Edward Park
(74) *Attorney, Agent, or Firm* — Myers Bigel, P.A.

(57) ABSTRACT

Disclosed is a method of measuring a refractive error using a reflection image of a pupil for a visible ray, the method capable of diagnosing and self-examining a refractive error using only an image captured by a smartphone camera. The method may include obtaining an image by projecting a visible ray, using a flash, onto the retina of a subject and capturing, using a smartphone camera, a shape and location of the image reflected in the pupil of the subject, applying the image to a residual neural network (ResNet) model trained using data of an ImageNet based on clinical information into which result values of a refractive error of the subjects have been incorporated, and outputting the refractive error of the image and a measurement factor measured to determine the refractive error based on the shape and the location reflected in the pupil in a process of deriving the refractive error of the image.

5 Claims, 3 Drawing Sheets

METHOD FOR MEASURING ANOMALIES OF REFRACTION USING A REFLECTION IMAGE OF PUPIL IN VISIBLE LIGHT

BACKGROUND

1. Technical Field

The present disclosure relates to a method of measuring a refractive error using a reflection image of a pupil for a visible ray, and particularly, to a method of measuring a refractive error, which can diagnose and self-examine a refractive error using only an image captured by a smartphone camera.

2. Related Art

A refractive error means a state in which light is not accurately focused on the retina due to several causes. In general, a refractive error includes myopia, hyperopia, astigmatism, and presbyopia. Since a refractive error that is not corrected makes an image blurred, the refractive error has a decisive effect on the development of eyesight of a newborn baby or an infant. Even in a newborn baby period, a newborn baby may lose his/her eyesight within one or two months after his/her birth due to congenital cataract. The blocking of the stimulus of light or the refractive error may be caused by an ophthalmologic disease, such as retinoblastoma, which may threaten the baby's life. Accordingly, early diagnosis and treatment for a proper eyesight correction and the prevention of amblyopia are essential. It is however very difficult to accurately diagnosis a refractive error in a newborn baby or an infant who rarely cooperates with the diagnosis and treatment.

If amblyopia is not treated at an early stage, it may be difficult for a person to have normal eyesight even after growing up. Furthermore, the person may have a difficulty in perceiving a 3D stereoscopic image because he or she has weak stereopsis or no stereopsis, and may have low accuracy and speed in holding a thing, walking, driving, or reading in daily life compared to normal eyesight.

A conventional standard inspection for confirming a refractive error in an infant includes a cycloplegic refraction for measuring a refractive error using a skiascope after applying cycloplegic eye drops. However, an oculist needs to perform the cycloplegic refraction, and there is a possibility that a measured value of the cycloplegic refraction may be inaccurate if an inspector is not skilled. Furthermore, there are problems in that there is a difficulty in performing an inspection on an infant because the cooperation of the patient is essential and the cycloplegic refraction is not suitable for an amblyopia group selection inspection due to a long inspection time. Furthermore, there are problems in that an accommodative force is slightly reduced due to an eye dropping effect, a pupil becomes large or a close objects becomes blurry, and a glare symptom remains after the inspection.

SUMMARY

Various embodiments are directed to providing a method of measuring a refractive error, which determines a degree of a refractive error by using a deep learning algorithm based on photorefraction using a smartphone camera.

In an embodiment, a method of measuring a refractive error using a reflection image of a pupil for a visible ray may include obtaining an image by projecting a visible ray using a flash onto the retina of a subject and capturing, using a smartphone camera, a shape and a location reflected in the pupil of the subject, applying the image to a residual neural network (ResNet) model trained using data of an ImageNet based on clinical information into which result values of a refractive error of the subjects have been incorporated, and outputting the refractive error of the image and a measurement factor measured to determine the refractive error in the shape and the location reflected in the pupil in a process of deriving the refractive error of the image.

In an embodiment, the obtaining of the image may include editing, in the form of a preset pixel, the image before the applying of the image to the ResNet model.

In an embodiment, the applying of the image may include extracting a feature vector from the image and applying the feature vector to the ResNet model.

In an embodiment, the training of the ResNet model using the data of the ImageNet may include grouping the refractive error of the clinical information into preset sections based on a diopter (D).

Furthermore, the outputting of the measurement factor may include representing, in the form of a heat map, the image of the pupil compared by the ResNet model in order to output the refractive error of the pupil.

DETAILED DESCRIPTION

Figure 1:
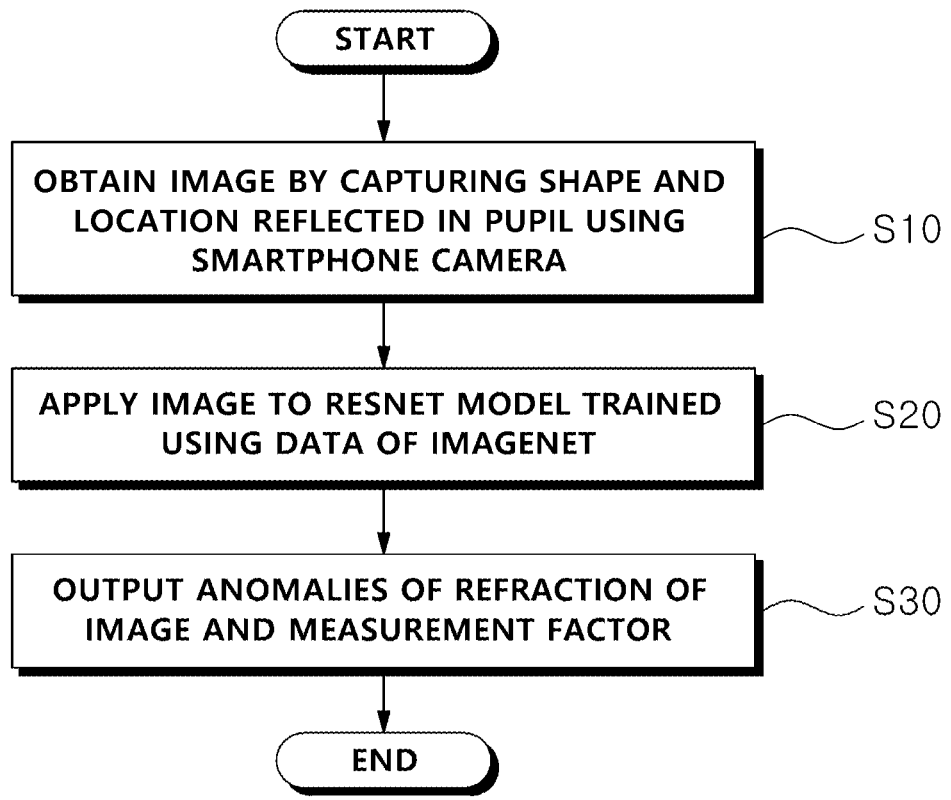
FIG. 1 illustrates a flowchart of a method of measuring a refractive error according to an embodiment of the present disclosure.

Terms used in this specification are briefly described, and the present disclosure is described in detail.

The terms used in the present disclosure are common terms currently and widely used by taking into consideration functions in the present disclosure, but the terms may be changed depending on an intention of a technician skilled in the art, a precedent, or the advent of a new technology. Furthermore, in a specific case, some terms are randomly selected by the applicant. In this case, the meaning of a corresponding term will be described in detail in the corresponding description of the invention. Accordingly, terms used in the present disclosure should be defined based on their substantial meanings and contents over the present disclosure, not the simple names of the terms.

In the entire specification, unless explicitly described to the contrary, the word "include" will be understood to imply the further inclusion of stated elements, not the exclusion of any other elements. Furthermore, the term unit " . . . unit" or "module" described in the specification means a unit for processing at least one function or operation, and the unit may be implemented by hardware or software or a combination of hardware and software. Furthermore, throughout the specification, when it is described that one part is "connected" to another part, the one part may be "directly connected" to the another part or may be "indirectly connected" to the another part "with a still another part interposed therebetween."

Hereinafter, embodiments of the present disclosure are described in detail with reference to the accompanying drawings, in order for a person having ordinary skill in the art to which the present disclosure pertains to easily carry out the present disclosure. The present disclosure may be implemented in various different ways, and is not limited to the disclosed embodiments herein. In the drawings, in order to clearly describe the present disclosure, a description of parts unrelated to the description is omitted, and similar reference numbers are used to refer to similar parts throughout the specification.

A method according to an embodiment of the present disclosure may be executed by an app implemented in a smartphone, and may be implemented in a device, on which a processor capable of executing a program for obtaining an image through reflected light is mounted, in addition to the smartphone. All processes of the method may be implemented as software and processed by a processor (not illustrated).

FIG. 1 illustrates a flowchart of a method of measuring a refractive error according to an embodiment of the present disclosure.

Referring to FIG. 1, the method according to an embodiment of the present disclosure may include step S10 of obtaining an image, step S20 of applying the image to a residual neural network (ResNet) model, and step S30 of outputting a refractive error and a measurement factor.

The step S10 of obtaining the image may include a process of projecting a visible ray, using a flash, onto the retina of a subject and capturing a shape and location of the image reflected in the pupil of the subject using a smartphone camera. The obtained image may be used as an input image.

The step S20 of applying the image to the ResNet model is a process of inputting the image to the ResNet model trained using the existing clinical information. The results of the input image may be output through clinical information into which result values of a refractive error of the subjects have been already incorporated.

The step S30 of outputting the refractive error and the measurement factor is a process of outputting the refractive error of the image and the measurement factor measured to determine the refractive error in the shape and location of the image reflected in the pupil in a process of deriving the refractive error of the image.

The present disclosure generally relates to an algorithm for automatically diagnosing a refractive error of an eye, and more particularly, to an algorithm for outputting a degree of a refractive error using a photorefraction photograph, obtained by a smartphone, as input. The algorithm may implement the ResNet, that is, a kind of deep learning network, and apply an image to the deep learning network pre-trained using collected photorefraction photographs and refractive error value data for each photograph obtained by a medical specialist through a cycloplegic refraction.

The algorithm is roughly divided into two parts, that is, a deep learning network module for extracting a feature from a photograph and outputting a degree of a refractive error, and a Grad-Cam module for representing, in the form of a heat map, which feature the deep learning network module has used for decision making.

When a user finally inputs, to the ResNet model, a photorefraction photograph captured by the smartphone, the algorithm may output a degree of a refractive error in the photograph and a heat map carefully watched by the user when diagnosing the degree of a refractive error.

Figure 2:
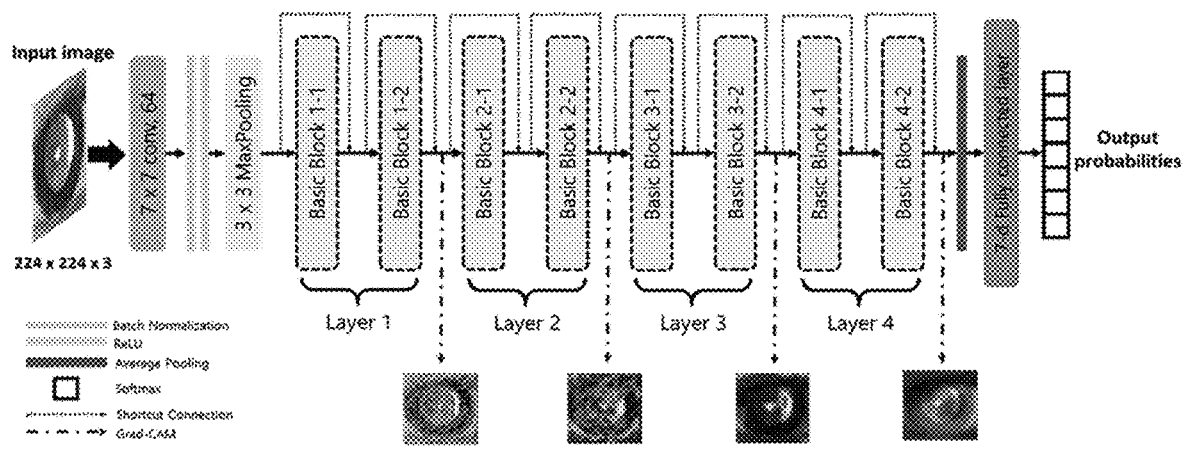
FIG. 2 illustrates a detailed configuration of the method of measuring a refractive error according to an embodiment of the present disclosure.

FIG. 2 illustrates a detailed configuration of the method of measuring a refractive error according to an embodiment of the present disclosure.

Referring to FIG. 2, the step of obtaining an image may further include the step of editing, in the form of a preset pixel, the image before the applying of the image to the ResNet model. The processor may extract a corneal reflex candidate from a received fundus oculi image and extract a pupil candidate from the extracted corneal reflex candidate.

The processor may generate an image by extracting a pupil portion of a fundus oculi image in a size of 224×224 from the pupil candidate using photorefraction.

The step of applying the image is a process of applying the image to the ResNet model. The process may include steps of extracting a feature vector from the image and applying the feature vector to the ResNet model.

The processor has been trained to implement a program based on the existing clinical information. The ResNet model refers to a model for reading a refractive error based on clinical information, and may be previously trained by matching, with each image, a refractive error value obtained through cycloplegic refraction.

In the training process, data for training, data for verification, and data for experiments may be matched to generate the ResNet model.

The data for training are data for training a deep learning network. The data for training are composed of pairs of photorefraction photographs, which do not overlap the data for verification and the data for experiments, and refractive error value data for each photograph obtained by a medical specialist through cycloplegic refraction.

The data for verification are data for evaluating accuracy of the deep learning network in the process of training the deep learning network using the data for training. The data for verification are composed of pairs of photorefraction photographs, which do not overlap the data for training and the data for experiments, and refractive error value data for each photograph obtained by a medical specialist through cycloplegic refraction.

The data for experiments are data for checking the final accuracy of the trained deep learning network. The data for experiments are composed of pairs of photorefraction photographs, which do not overlap the data for training and the data for verification, and refractive error value data for each photograph obtained by a medical specialist through cycloplegic refraction.

The step of training the ImageNet model using data of the ImageNet may further include a step of grouping the refractive error of the clinical information into preset sections based on a diopter (D).

In this case, the data for training, the data for verification, and the data for experiments have a ratio of 6:2:2. The refractive error values may be dividedly set as seven sections as in Table 1 below. A photograph may be classified for each set section.

TABLE 1

| Refractive error degree (D = Diopter) | Accuracy (%) |
| --- | --- |
| ≤−5.0 D | 80.0 |
| >−5.0, ≤−3.0 D | 77.8 |
| >−3.0, ≤−0.5 D | 82.0 |

TABLE 1-continued

| Refractive error degree (D = Diopter) | Accuracy (%) |
|---|---|
| >−0.5, <+0.5 D | 83.3 |
| ≥+0.5, <+3.0 D | 82.8 |
| ≥+3.0, <+5.0 D | 79.3 |
| ≥+5.0 D | 75.0 |
| Total | 81.6 |

The ResNet (e.g., 18 layers) model trained using data of the ImageNet is invoked as an initial model. The last layer of the 18 layers may be replaced with a seven-dimensional fully-connected layer.

Furthermore, the ResNet of the seven-dimensional fully-connected layer is repeatedly trained up to 500 times using the data for training and the data for verification. Such training is stopped when the accuracy of the ResNet model converges on the data for verification.

In this case, a loss function used for the training is cross-entropy of a degree of a refractive error probability value predicted by the ResNet (e.g., the ResNet may be trained as a deep learning framework called Pytorch which is a deep learning library).

The step of outputting the measurement factor may include a step of representing, in the form of a heat map, the image of the pupil compared by the ResNet model in order to output a refractive error of the pupil.

In an embodiment, the accuracy of the trained ResNet model may be finally checked based on the data for experiments. In this case, an explanation power of the ResNet model may be increased by making the heat map using the Grad-CAM algorithm.

The heat map and the Grad-CAM algorithm may be used to verify whether the deep learning network has predicted a degree of a refractive error based on a proper ground for determinations by checking the heat map formed by the Grad-CAM algorithm again upon diagnosis.

The ResNet the model (e.g., 18 layers) trained using data of the ImageNet is invoked as an initial model from Pytorch. The last layer may be replaced with the seven-dimensional fully-connected layer.

Figure 3:
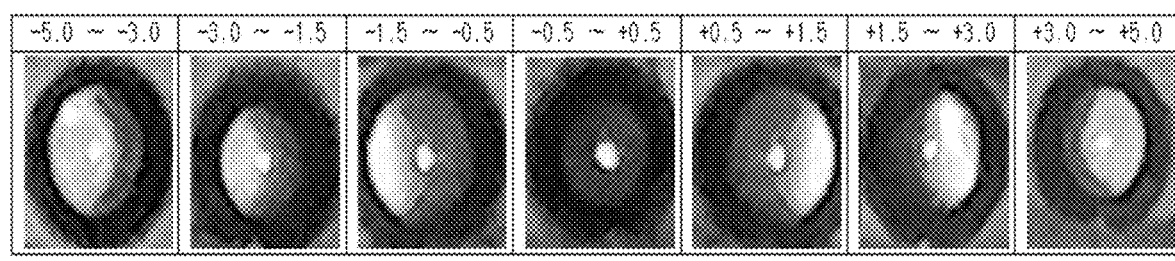
FIG. 3 illustrates that a refractive error are measured in the form of eyeball reflection according to an embodiment of the present disclosure.

FIG. 3 illustrates that a refractive error are measured in the form of eyeball reflection according to an embodiment of the present disclosure.

From FIG. 3, shapes of eyeball reflection according to degrees of the refractive error can be seen in relation to Table 1.

If a refractive error is measured as in FIG. 3, an inspection can be performed within a short time, and measurement with high accuracy can be performed on an infant patient who rarely cooperates with the measurement.

Furthermore, eyesight developmental retardation attributable to a refractive error can be diagnosed at an early stage.

Clinical trial results of prototype according to an embodiment of the present disclosure are described as follows. Table 2 below illustrates the results obtained by measuring degrees of a refractive error in astigmatism, hyperopia, anisopia, and myopia according to ages of an infant.

TABLE 2

| Degrees of a refractive error which may cause eyesight developmental retardation (e.g., amblyopia) | | | | |
|---|---|---|---|---|
| age, months | astigmatism | hyperopia | anisopia | myopia |
| 12-30 | >2.0 D | >4.5 D | >2.5 D | >−3.5 D |
| 31-48 | >2.0 D | >4.0 D | >2.0 D | >−3.0 D |
| >48 | >1.5 D | >3.5 D | >1.5 D | >−1.5 D |

Table 3 below illustrates results obtained by measuring degrees of a refractive error in astigmatism, hyperopia, anisopia, and myopia according to ages of an infant using the measurement method according to an embodiment of the present disclosure.

TABLE 3

| Criterion for evaluation (e.g., cycloplegic refraction) | | |
|---|---|---|
| | Positive (+) | Negative (−) |
| Positive (+) | True positive (A) | False positive (B) |
| Negative (−) | False negative (C) | True negative (D) |
| Drop-out rate | E | F |

Sensitivity=$A/(A+C)*100(\%)$

Specificity=$D/(B+D)*100(\%)$

Positive expectation=$A/(A+B)*100(\%)$

Negative expectation=$D/(C+D)*100(\%)$

Drop-out rate=$(E+F)/(A+B+C+D+E+F)$

Table 3 illustrates that the measured refractive error value degree is compared with a Gold standard of a refractive error called "cycloplegic refraction."

Clinical trial results of amblyopia diagnosis accuracy for a corresponding device are obtained by comparing amblyopia diagnosis using the corresponding device with amblyopia diagnosis using cycloplegic refraction.

Table 4 below illustrates the evaluation of amblyopia risk performance indices.

TABLE 4

| Evaluation of amblyopia risk performance index | |
|---|---|
| Sensitivity | 80.49 |
| Specificity | 74.17 |
| Positive expectation | 68.04 |
| Negative expectation | 84.76 |
| Accuracy | 76.73 |
| Drop-out rate | 3.12 |

From Table 4, it may be seen that the sensitivity of a amblyopia patient which can be screened by a corresponding technology is 80.49%, specificity of a patient having no amblyopia, which can be diagnosed not to have the disease by a corresponding technology, is 74.17%, and a drop-out rate at which the inspection results are not derived based on all patients is 3.12%, that is, the sensitivity and specificity are very high and the drop-out rate is very low.

According to the present disclosure having the aforementioned construction, there are advantages in that a refractive power measurement time is short and a refractive error can be measured even without the cooperation of a subject.

Furthermore, the present disclosure has advantages in that both eyes can be inspected at the same time without using cycloplegic and particularly, the present disclosure is conveniently used if lots of groups are examined.

Furthermore, the present disclosure has an advantage in that a degree of errors of semiquantitative refraction, such as myopia, hyperopia, or astigmatism, an accommodative force, whether a subject has phoria or amblyopia, and an ophthalmologic disease that may cause opaque media, such as cataract, can be diagnosed.

Furthermore, the present disclosure has advantages in that eyes can be relatively easily inspected at an inexpensive price without expensive equipment because the light source and camera of a smarphone are used and equity to local medical access can be improved in a medical backwater not having an oculist.

Although the present disclosure has been described in detail above through the representative embodiments, a person having ordinary skill in the art to which the present disclosure pertains will understand that the embodiments may be modified in various ways without departing from the category of the present disclosure. Accordingly, the scope of rights of the present disclosure should not be limited to the aforementioned embodiments, but should be defined by all changed or modified forms derived from the appended claims and equivalent concepts thereof.

What is claimed is:

1. A method of measuring a refractive error using a reflection image of a pupil for a visible ray, the method comprising:

obtaining an image by projecting a visible ray, using a flash, onto a retina of a subject and capturing, using a smartphone camera, a shape and location of the image reflected in the pupil of the subject;

applying the image to a residual neural network (ResNet) model trained using data of an ImageNet based on clinical information into which result values of a refractive error of the subjects have been incorporated; and outputting the refractive error of the image and a measurement factor measured to determine the refractive error based on the shape and the location reflected in the pupil in a process of deriving the refractive error of the image.

2. The method of claim 1, wherein the obtaining of the image comprises editing, in the form of a preset pixel, the image before the applying of the image to the ResNet model.

3. The method of claim 1, wherein the applying of the image comprises:

extracting a feature vector from the image; and applying the feature vector to the ResNet model.

4. The method of claim 1, wherein the training of the ResNet model using the data of the ImageNet comprises grouping the refractive error of the clinical information into preset sections based on a diopter (D).

5. The method of claim 1, wherein the outputting of the measurement factor comprises representing, in the form of a heat map, the image of the pupil compared by the ResNet model in order to output the refractive error of the pupil.

* * * * *